United States Patent [19]
Mizushima et al.

[11] Patent Number: 5,942,242
[45] Date of Patent: Aug. 24, 1999

[54] MEDICAMENTS FOR NASAL ADMINISTRATION

[75] Inventors: Yutaka Mizushima, Tokyo; Yasuo Kosaka, Matsudo; Kayoko Hosokawa; Ryozo Nagata, both of Kumamoto; Megumu Higaki; Rie Igarashi, both of Kawasaki; Tetsuo Ebata, Kunitachi, all of Japan

[73] Assignee: LTT Institute Co., Ltd, Kanagawa-Pref., Japan

[21] Appl. No.: 08/679,161

[22] Filed: Jul. 10, 1996

[30] Foreign Application Priority Data

Jul. 12, 1995 [JP] Japan .................................. 7-197919

[51] Int. Cl.$^6$ .............................. A61F 13/00; A61F 2/00; A61K 38/00; A61K 47/00
[52] U.S. Cl. ........................ 424/434; 424/435; 424/436; 424/426; 424/428; 424/430; 424/464; 424/469; 424/499; 424/501; 424/497; 514/2; 514/772.3; 514/777; 514/778; 514/937
[58] Field of Search ..................... 424/426, 428, 424/430, 434, 435, 436, 437, 464, 469, 499, 501, 45, 473, 497; 514/772.3, 777, 778, 937, 960, 967, 947, 3, 4, 12, 13–15, 2

[56] References Cited

U.S. PATENT DOCUMENTS

| | | | |
|---|---|---|---|
| 5,112,804 | 5/1992 | Kowarski | 514/3 |
| 5,158,761 | 10/1992 | Kamishita et al. | 424/45 |
| 5,204,108 | 4/1993 | Illum | 424/434 |
| 5,342,922 | 8/1994 | Marshall et al. | 530/329 |
| 5,397,771 | 3/1995 | Bechgaard et al. | 514/2 |
| 5,554,388 | 9/1996 | Illum | 424/501 |

OTHER PUBLICATIONS

Maarten A.J.M. Jacobs, Robien H. Schreuder, Kenneth Jap–A–Joe, Jos J. Nauta, Peder M. Andersen and Robert J. Heine,"The Pharmacodynamics and Activity of Intranasally Administered Insulin in Healthy Male Volunteers," *Diabetes*, vol. 42, Nov. 1993, 7 pages.

K. Drejer, A. Vaag, K. Bech, P. Hansen, A.R. Sorensen, and N. Mygind, "Intranasal Adminstration of Insulin With Phospholipid as Absorption Enhancer: Pharmacokinetics in Normal Subjects," *Diabetic Medicine*, vol. 9, 1992; pp. 335–340.

*Primary Examiner*—Lynette R. F. Smith
*Assistant Examiner*—Dat Quan Lee
*Attorney, Agent, or Firm*—Price, Heneveld, Cooper, Dewitt & Litton

[57] ABSTRACT

A medicament for nasal administration to be used for disease prevention or treatment comprising a vaccine or a pharmacologically active peptide compounded with an ion exchange resin or adsorbent resin powder whose mean particle size is not larger than 200 $\mu$m.

19 Claims, 2 Drawing Sheets

MEDICAMENTS FOR NASAL ADMINISTRATION

BACKGROUND OF THE INVENTION

1. Field of the Invention

The present invention relates to medicament compositions for nasal administration of vaccines, pharmacologically active peptides such as peptide hormones, physiologically active proteins, or enzyme proteins.

2. Description of the Related Art

In recent years, new vaccines and pharmacologically active peptides have been produced with increasing frequency in accordance with the progress of molecular biology and peptide synthesis techniques. Vaccine research efforts have worked to support the extensive diphtheria, pertussis, polio, measles, and tuberculosis vaccination programs carried out in developing countries. In particular, research on infant vaccines has worked: (1) to reduce side-effects, to enhance quality control, and to improve mucosal immunity through non-injected vaccine administration methods; (2) to develop slow-releasing adjuvants for use in single-administration vaccines; (3) to produce heat-resistant live vaccines so as to preserve their activity (40° C., 3 weeks); and (4) to develop mixed vaccines.

Vaccine research efforts in developed countries have focused on the production of novel influenza vaccines, especially in response to the needs of geriatric medicine. While vaccines are regularly administered to a wide variety of patients, essentially only one method of administration has been employed: subcutaneous injection. This is because effective immunological resistance has not been reliably produced by means of oral, percutaneous, rectal, or hypoglossal administration due to the physical properties of those tissue types.

Nasal administration of component vaccines has been anticipated as a desirable and convenient method, where satisfactory immunological resistance has not been obtained by means of conventional antigen administration methods.

Pharmacologically active peptides, such as insulin, calcitonin, elcatonin, salmon calcitonin, buserelin acetate (Gn-RH derivatives), leuprorelin acetate (LH-RH derivatives), somatropin, and glucagon, are medicines indispensable for the treatment of many fatal or serious diseases. However, all of these are poorly absorbed through the normal gastro-intestinal, rectal, or hypoglossal mucosa, or the skin. Furthermore, they are deactivated by proteases in the digestive system. Therefore, pharmacological effects by means of oral, percutaneous, gastro-intestinal, or hypoglossal administration thereof are hardly expected. Accordingly, insulin, buserelin acetate, and leuprorelin acetate are administered subcutaneously, while elcatonin and calcitonin are injected intramuscularly.

Administration by means of injection, particularly, subcutaneous injection, considerably harms the quality of life of patients, because of the frequent infliction of pain with repeated injections which are required in many cases due to quick metabolism of the agent in the body. Therefore, convenient methods of administration, such as oral, ophthalmic, and nasal administration are preferable when effective, since repeated injection is not only harmful to the skin of the patient, but also increases the risk of injection with contaminated needles and compounds the problem of contaminated medical waste disposal.

Recently, it has been recognized that it would be highly beneficial to develop non-injection administration methods for patients to repeatedly self-administer vaccine- or pharmacologically active peptide-based medicines and thereby prolong the pharmacological effects thereof. However, it has generally been found difficult to produce pharmacologically effective, bioavailable levels of peptide-based medicines by means other than injection, such as oral, percutaneous, gastro-intestinal, rectal, or subcutaneous administration. Based on this observation, nasal administration has been tried as a means of achieving pharmacologically effective levels of peptide-based medicines. As a result, several commercial, solution- or suspension-based nasal spray products have become available. Most of these, however, produce only local irrigation, sterilization, analgesic, or anti-inflammatory effects.

Nasal administration methods which induce systemic effects have been studied with respect to various medicines, but with little practical outcome so far because they do not provide sufficient absorption to produce systemic pharmacological effects, they cause irritation to the nasal mucosa, they produce unpleasant odors, and the active component of the medicines is unstable in the nasal cavity.

However, with regard to calcitonin, effective nasal sprays and freon-gas-propelled suspension sprays have been developed, and buserelin nasal drops have also been marketed. This approach has been successful for those two peptides because they are directly absorbed by the capillaries supplying the nasal mucosa and are thus transferred into the general circulation, thereby producing their pharmacological effects. Nevertheless, these active peptide products are likewise not satisfactory in that they irritate the mucosa and do not allow efficient absorption to be sustained. With reference to the nasal drops, leakage from the nasal cavity after administration remains a significant shortcoming.

SUMMARY OF THE INVENTION

Brief Summary of the Invention

The present invention relates to medicament compositions for nasal administration of vaccines, peptides, proteins, or enzymes comprising a vaccine, a pharmacologically active peptide such as a peptide hormone, physiologically active protein, or enzyme protein, or mixtures thereof, and an ion exchange resin or an adsorbent resin powder as carrier therefor which effectively delivers the vaccine or peptide to, and supports its transfer across, the surface of the nasal mucosa for absorbtion into the general circulation.

Recognizing that it is essential to transfer the vaccine or active peptide to the surface of the nasal mucosa to be absorbed into the general circulation, we have succeeded in finding, by extensive research, certain ion exchange resins and adsorbent resins which are effective as powdered carriers for transferring vaccines or active peptides to the nasal mucosa where they are easily released, and which are inactive and harmless to the human body, and which contain no harmful impurities. In particular, cation exchange resins have been found appropriate as carriers for acid proteins such as insulin, wherein the negatively charged cation exchange resin easily releases or repels such acid proteins upon their becoming negatively-charged in solution.

The present invention thus sets forth a safe and easy-to-handle medicament for nasal administration which exhibits superior clinical effects as a result of improved transmembrane vaccination and enhanced systemic absorption of the peptide thereby.

Object of the Invention

In accordance with one aspect of the invention, the present invention comprises a carrier which delivers the vaccine or the active peptide to the nasal mucosa, where an active component of the medicine is released and absorbed into the general circulation.

In accordance with another aspect of the invention, the invention comprises a resin powder whose mean particle size is not greater than 200 μm, which is readily sprayed and gives minimal sensation of any foreign matter.

In accordance with still another aspect of the invention, the invention also comprises a perfume or fragrance to facilitate patients' receptiveness and/or a stabilizing agent to obtain medicinal stability.

DETAILED DESCRIPTION OF THE PREFERRED EMBODIMENTS

The method used for compounding a vaccine or pharmacologically active peptide with a carrier is not specifically limited except in so far as it provides uniform and stable mixing. Such methods include: (1) preparing a suspension by adding an ion exchange resin or adsorbent resin powder to a vaccine solution or suspension; (2) mixing a dried vaccine or pharmacologically active peptide with an ion exchange resin or adsorbent resin powder by means of a mortar or ball mill while maintaining an appropriate relative humidity; (3) freeze drying a suspension obtained by method (1); and (4) increasing the homogeneity of a mixture of method (2) by adding an organic solvent such as ethanol.

The ion exchange resin to be used in the present invention is selected from the group including: polystyrenes, methacrylic resin, acrylic resins, phenol-formaldehyde resins, cellulose polymers, dextran polymers, and mixtures thereof. Examples of such polymers include, sodium polystyrenesulfonate prepared according to the Pharmacopeia of Japan, calcium polystyrenesulfonate prepared according to the Pharmacopeia of Japan, Amberlite® IRP64, Amberlite® CG-50, Amberlite® DP-1, and Dowex® 2, and mixtures thereof, which bear as cation exchange functional groups, sulfonic acid or carboxylic acid, or a salt thereof, e.g., a sodium, potassium, or calcium salt. The anion exchange resins include, for example, quaternary ammonium resin derivatives or, e.g., chloride, salts thereof. Examples of such chloride salts include cholestyramine, Amberlite® IRP67, Amberlite® IRA-68, Dowex® 50w, and mixtures thereof.

Examples of adsorbent resins include styrenedivinylbenzenes, such as: Diaion® HP10; Diaion® HP20; Sepabead 207; Amberlite® XAD2; Lewatit® OC1031; Dolite® ES861; methacrylic acid esters, such as Diaion® HP2MG and Amberlite® XAD-7; polyethylenes; vinyl chloride resins; amino acid sulfoxides; and mixtures thereof.

The mean particle size of the ion exchange resin or the adsorbent resin of the present invention is not larger than 200 μm, more preferably 10 to 150 μm, and still more preferably 40 to 70 μm. It is favorable that the particle size of the vaccine or peptide to be used in the present invention be as small as possible in order to facilitate absorption through the nasal mucosa. The mean particle size is preferably not larger than 30 μm, and more preferably not larger than 20 μm.

The total amount of the powdered medicament to be administered into the human nasal cavity as a single dose is approximately 5 to 50 mg, preferably 10 to 30 mg, more preferably 15 to 25 mg. In this case, the total amount is the sum of the amount of a vaccine or pharmacologically active peptide and that of the carrier. As for the medicament in the form of a suspension, the amount for a single dose is 0.1 to 2.5 ml, preferably 0.2 to 2.0 ml, more preferably 0.3 to 1.5 ml. In this case, there is no specific limitation on the mixing ratio of the medicine and the carrier.

Table 1 illustrates as examples the kinds of vaccines preferably used in the present invention and the corresponding effective doses thereof. Besides these can be mentioned a vaccine for Weil's disease.

| Vaccine | Single Effective Dose (compounded with 5 to 50 mg of carrier) |
|---|---|
| Diphtheria | 6 to 120 Lf |
| Pertussis | 4 to 16 IU |
| Measles | 5,000 to 20,000 $TCID_{50}$ |
| German Measles | 1,000 to 4,000 $TCID_{50}$ |
| Influenza | 70 to 1,300 CCA |
| Japanese Encephalitis | 0.25 to 2.0 ml |
| Cholera | 4 to 8,000,000,000 particles |
| Parotitis | 5,000 to 20,000 $TCID_{50}$ |
| Varicella | 1,000 to 4,000 PFU |
| B-type Hepatitis | 10 to 80 μg |
| Tetanus | 5 to 20 Lf |
| BCG | 12 to 320 mg |

There is no particular limitation on which active peptides may be used in the present invention except insofar as they can be nasally administered and are not irritating to the nasal mucosa. These include: insulin; glucagon; calcitonin; gastrin; parathyroid hormones; angiotensin; growth hormones; secretin; luteotropic hormones (prolactin); thyrotropic hormones; melanocyte-stimulating hormones; thyroid-stimulating hormones (thyrotropin); luteinizing-hormone-stimulating hormones; vasopressin; oxytocin; protyrelin; peptide hormones such as corticotropin; growth-hormone-stimulating factor (somatostatin); G-CSG, erythropoietin; EGF; physiologically active proteins, such as interferon and interleukin; SOD and derivatives thereof; enzymes such as urokinases and lysozymes; and mixtures thereof.

Table 2 lists as examples the kinds of pharmacologically active peptides preferably used in the present invention and the corresponding doses thereof.

| Active Peptide | Single Effective Dose (compounded with 5 to 50 mg of carrier) |
|---|---|
| Insulin | 4 to 80 units |
| Calcitonin | 10 to 320 units |
| Elcatonin | 10 to 320 units |
| Salmon Calcitonin | 10 to 320 units |
| Buserelin Acetate (Gn-RH derivative) | 0.1 to 0.5 mg |
| Leuprorelin Acetate (LH-RH derivative) | 0.1 to 0.5 mg |
| Somatropin | 4 to 60 IU |
| Glucagon | 0.25 to 5 mg |

When the medicinal component contained in the medicament of the present invention needs to be stabilized, or when increasing the total volume is required because the amount of the active component is too small to handle correctly, gelatin, gelatin succinate, degradated gelatin, proteins such as human serum albumin, amino acids such as aspartic acid, or sugars such as mannitol may be added to the medicament of the present invention. The methods for adding such agents are not specifically limited, nor is the mixing ratio thereof specifically limited.

In addition, the present invention may include 0.1 to 2% by weight of smoothing agents such as talc, leucine, or magnesium stearate to increase the "flowability" of the powder.

To increase both adherence to the nasal mucosa and the stability of the suspension, the present invention may include a water-soluble polymer powder, such as: polyacrylic acid or polymethacrylic acids or metal salts, such as sodium salt or potassium salts, thereof, with a mean particle size of 0.5 to 200 $\mu$m, preferably 20 to 100 $\mu$m; a water-soluble acrylate polymer such as polyacrylamide, having a molecular weight of 30,000 or greater, preferably 50,000 to 10,000,000; carboxyvinyl polymers, methylcelluloses, ethylcelluloses, hydroxymethylcelluloses, hydroxypropylmethylcelluloses, carboxymethylcelluloses, carboxymethylchitin, polyvinylpyrrolidone, polyvinylalcohols, ester gums, polybutene, synthetic hydroxypropyl-starch, synthetic carboxymethyl-starch, synthetic polyvinylethers, and polyethylene oxide, having an average molecular weight of 20,000 to 9,000,000, and preferably 100,000 to 7,000,000; natural polymers such as hyaluronic acid, sodium alginate, gelatin, gluten, carboxymethyl-starch, hydroxypropyl-starch, gum arabic, mannan, dextran, tragacanth, amylopectin, xanthan gum, locust bean gum, casein, polyvinylethers, and pectin; and mixtures thereof.

The medicament powder of the present invention may be administered as a non-water suspension or ointment by being added to hydrocarbons such as Vaseline, fatty acid glycerin esters, or to polyhydric alcohols such as glycerin.

Furthermore, a medicament of the present invention may be flavored with sugars, amino acids, or organic acids. It may also include water-soluble acids, bases, or salts thereof, or chelating agents for stabilizing the physiologically active peptides.

Embodiment 1. Nasal Administration to Rabbit of an Insulin Medicament of the Present Invention Preparation: 40 mg of insulin powder and 200 mg of carrier powder were placed into an agate mortar, and then uniformly mixed for 10 min. at 30–40% relative humility. Another 200 mg of the carrier was added and mixing continued for another 20 min., followed by the addition of 560 mg of the carrier and another 20 min. of mixing to produce the medicament of the present invention. An amount corresponding to 25 units of insulin was encapsulated in gelatin to be used as a sample. This procedure was followed in each of three runs. The carriers used in each run are as follows:

RUN I: sodium polystyrenesulfonate having a mean particle size of 40 $\mu$m, prepared in accordance with the Pharmacopoeia of Japan.

RUN II: calcium polystyrenesulfonate having a means particle size of 55 $\mu$m.

RUN III: styrenedivinylbenzene having a mean particle size of 45 $\mu$m (Diaion HP10).

Experiment: 8 rabbits (Std:NZW, male, 11-week-old, weight of 2.80 to 3.21 kg) were selected by an insulin sensitivity test (wherein 1 IU/kg of a short acting insulin was subcutaneously injected) and were then tranquilized by subcutaneous administration of 3 mg/kg of diazepam. A PABULIZER, modified for rabbits, (made by Teijin Limited) was used to nasally administer the sample to each one. Control rabbits were subcutaneously injected with insulin solution (3 IU/rabbit). Blood was collected from auricular veins before administration and 15, 30, 45, 60, 90, 120, 150, 180, 240, 300, 360 min. after the administration, and plasma insulin and blood sugar concentrations were measured. Blood sugar concentrations were measured with a portable electrode-type instrument (TOECHO SUPER II made by KDK Corporation/MARION MERRELL DOW K.K.).

Result: Experimental results according to change in serum insulin concentration are presented in FIG. 1.

Figure 1:
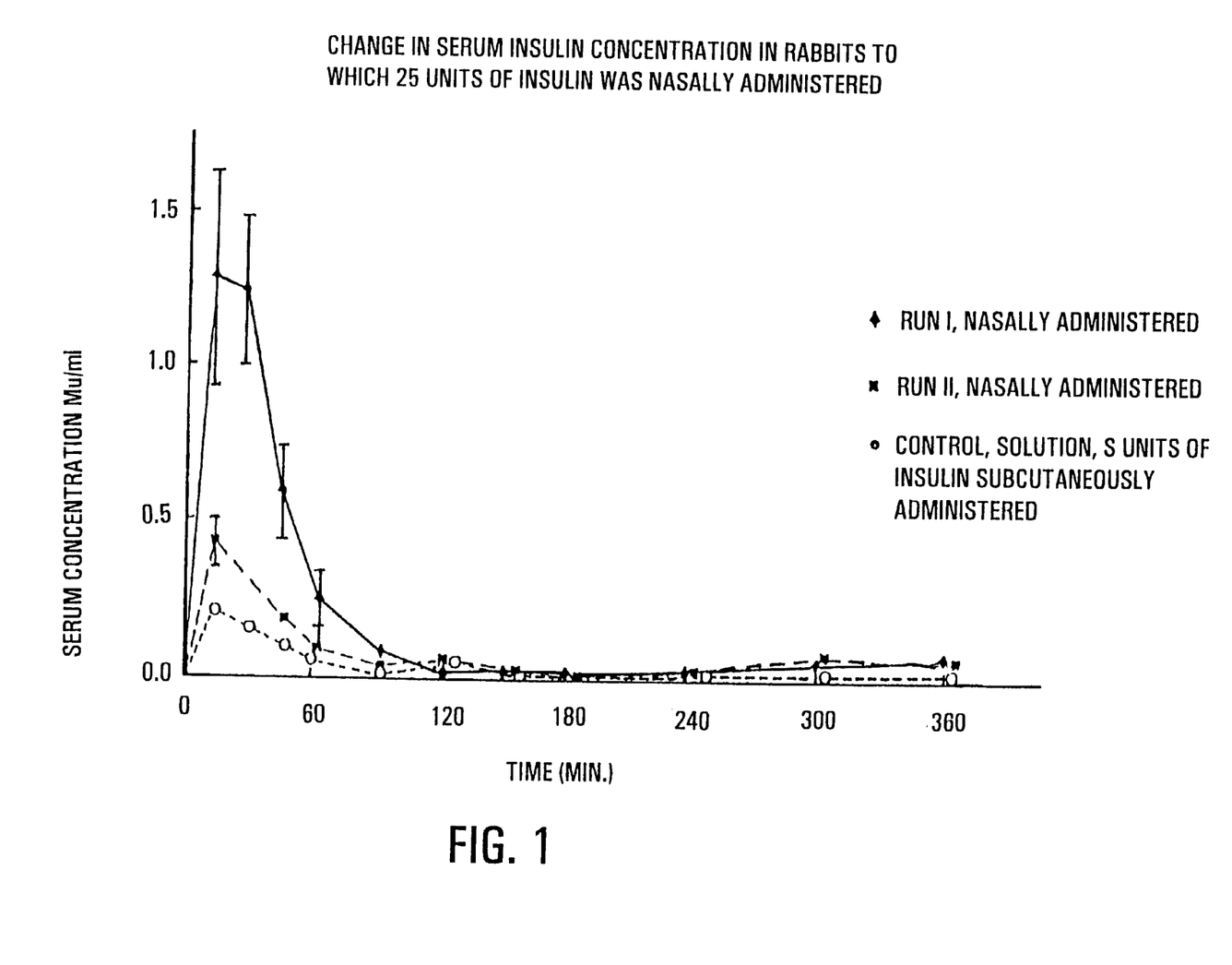
FIG. 1 is a graph of serum insulin concentration over time produced by nasal administration with medicament compositions embodying the present invention as compared with that produced by the traditional injection method.
Figure 2:
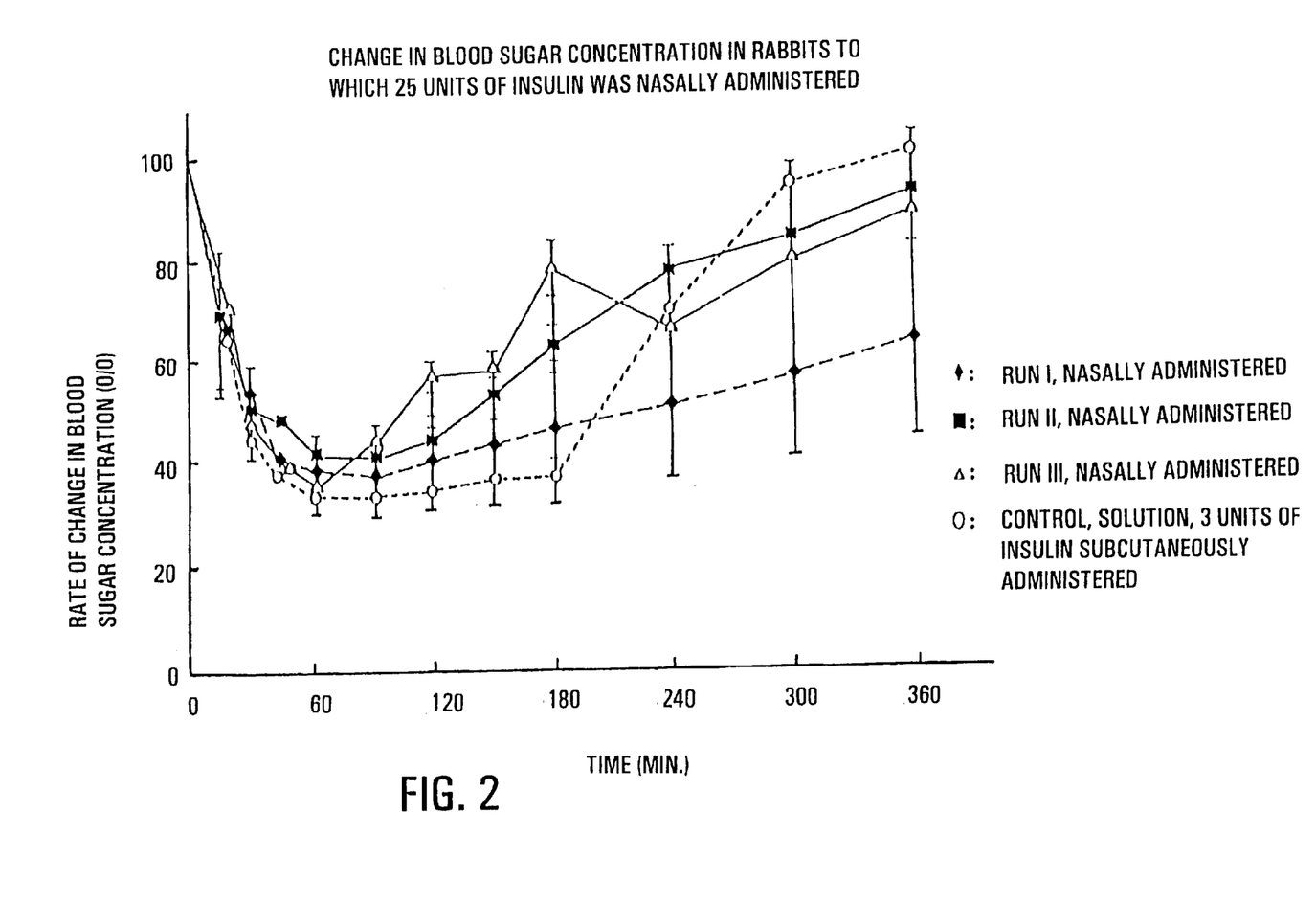
FIG. 2 is a graph of blood sugar concentration over time resulting from treatment with insulin by nasal administration of medicament compositions embodying the present invention as compared with that resulting from treatment by the traditional injection method.

Conclusion: As is shown in FIG. 1, nasal administration of the medicament of the present invention using sodium polystyrenesulfonate prepared in accordance with the Pharmacopoeia of Japan, calcium polystyrenesulfonate, or styrenedivinylbenzene (Diaion® HP10; not shown) enabled absorption of insulin, which was transferred to the general circulation. The remarkable decrease in blood sugar concentration due to the insulin is shown in FIG. 2.

Embodiment 2. Nasal Administration to Mouse of an Influenza Vaccine Medicament of the Present Invention Preparation: A water suspension was obtained by mixing for 1 hr., 10 $\mu$l of influenza antigen solution (2.15 mg/ml crude HA protein in purified water) and 20 $\mu$l of an 0.5 g/ml carrier suspension of sodium polystyrenesulfonate prepared in accordance with the Pharmacopoeia of Japan, having a mean particle size of 40 $\mu$m, or of calcium polystyrenesulfonate having a mean particle size of 45 $\mu$m.

Experiment: Three groups of 10 mice each (Balb/c, female, 6 to 8 week-old) were used. To the first group was nasally administered 1 $\mu$m of antigen solution alone, while to the second and the third groups, 3 $\mu$l of sodium polystyrenesulfonate or calcium polystyrenesulfonate vaccine suspension, respectively. Four weeks after administration, blood was collected from the heart, and serum was separated therefrom. At the same time, the nasal cavity was washed with 1 ml of PBS. Subsequently, total immunoglobulins (IgG, IgM, IgA) and HA protein-specific antibodies (IgA, IgG) contained in each serum and nasal wash sample were quantitatively determined by means of an enzyme-antibody method (ELISA).

Results: Quantitative results of specific HA-IgA are shown in Table 3.

TABLE 3

Immune Response in Mice to Which Influenza Vaccine was Nasally Administered HA-specific IgA*

|  | Nasal Sample | Serum |
| --- | --- | --- |
| HA alone (control) | <2 | <2 |
| HA + Sodium polystyrenesulfonate | $2^5$ | $2^3$ |
| HA + Calcium polystyrenesulfonate | $2^3$ | $2^2$ |

*Dilution factor designating ELISA positive (OD < 0.3)

Conclusion: Nasal administration of vaccine employing as carrier an ion exchange resin such as sodium polystyrenesulfonate or calcium polystyrenesulfonate brings about a high immune response, as indicated in Table 3. The nasally administered medicament of the present invention may be used as an effective preventative for measles, pertussis, diphtheria, etc., as well as for influenza.

EXAMPLES

The following examples illustrate the formulation and use of the medicament of the present invention, but do not serve to limit the scope of the invention in any way.

Example 1

An aqueous suspension was obtained by mixing for 1 hr., 2 L of influenza solution 2.15 mg/ml crude HA influenza antigen protein in purified water, and 4 L of a carrier suspension (0.5 g/ml sodium polystyrenesulfonate powder, prepared in accordance with the Pharmacopoeia of Japan, in purified water). For a single dose, 0.6 ml of this suspension is sprayed or administered by drops into the human nasal cavity.

Example 2

An aqueous suspension was obtained by mixing for 2 hrs., 2 L of diphtheria vaccine suspension (about 30 lf/ml diphtheria toxoid with aluminum salt) and calcium polystyrenesulfonate powder (mean particle size: 30 $\mu$m) to a final concentration of 0.5 g/ml of carrier. For a single dose, 1 ml of this suspension is sprayed or administered by drops into the human nasal cavity.

Example 3

Into an agate ball mill mortar were placed a freeze-dried powder of live measles vaccine ($4\times10^9$TCID$_{50}$) and 200 g of sodium polystyrenesulfonate powder prepared according to the Pharmacopoeia of Japan (mean particle size: 40 $\mu$m), and the resulting mixture was uniformly stirred for 10 min. at a relative humidity of 20 to 30%. Then 200 g additional carrier powder was added thereto, with stirring for 20 min., followed by 560 g more of this carrier powder and another 20 min. of stirring to produce a medicament of the present invention. Approximately 25 mg (corresponding to 10,000 TCID$_{50}$) of this mixture was encapsulated in a hard gelatin capsule (capsule No. 4 of the Pharmacopoeia of Japan), which was wrapped in PTP, and placed in an aluminum bag. This medicament is sprayed into the human nasal cavity.

Example 4

Into an agate ball mill mortar were placed a freeze-dried powder of live attenuated mumps vaccine ($2.8\times10^9$ TCID$_{50}$) and 200 g of styrenedivinylbenzene (Diaion® HP10) powder (mean particle size: 40 $\mu$m), and the resulting mixture was uniformly stirred for 10 min. at a relative humidity of 20 to 30%. Then 200 g additional carrier powder was added thereto, with stirring for 20 min., followed by 560 g more of this carrier powder and another 20 min. of stirring to produce a medicament of this invention. Approximately 25 mg (corresponding to 7,000 TCID$_{50}$) of this mixture was encapsulated in a hard gelatin capsule (capsule No. 4 of the Pharmacopoeia of Japan), which was wrapped in PTP, and placed in an aluminum bag.

Example 5

An aqueous suspension was obtained by mixing for 1 hr., 2 L of cholera vaccine suspension (2,000,000,000 particles/0.5 ml of S-type cholera vibrio of both Ogawa- and Inaba-type) with sodium polystyrenesulfonate powder prepared in accordance with the Pharmacopoeia of Japan (mean particle size: 40 $\mu$m) to a final concentration of 0.5 g/ml of carrier. For a single dose, 0.6 ml of this suspension is sprayed or administered by drops into the human nasal cavity.

Example 6

Into an agate ball mill mortar were placed a dried powder of live attenuated varicella vaccine ($1.2\times10^9$PFU) and 200 g of calcium polystyrenesulfonate powder (mean particle size: 40 $\mu$m), and the resulting mixture was uniformly stirred for 10 min. at a relative humidity of 30 to 40%. Then 200 g additional carrier powder was added thereto, with stirring for 20 min., followed by 560 g more of this carrier powder and another 20 min. of stirring to produce a medicament of this invention. About 25 mg (corresponding to 3,000 PFU) of this mixture was encapsulated in a hard gelatin capsule (capsule No. 4. of the Pharmacopoeia of Japan), which was wrapped in PTP, and placed in an aluminum bag.

Example 7

An aqueous suspension was obtained by mixing for 1 hr., 2 L of Japanese encephalitis vaccine suspension (also containing 200,000,000 Type-B cholera vibrio particles of the Inaba- and Ogawa-type) with sodium polystyrenesulfonate powder prepared in accordance with the Pharmacopoeia of Japan (mean particle size: 40 $\mu$m); to a final concentration of 0.5 g/ml of carrier. For a single dose, 1 ml of this suspension is sprayed or administered by drops into the human nasal cavity.

Example 8

An aqueous suspension was obtained by mixing for 1 hr., 2 L of tetanus toxoid suspension (10 Lf/ml tetanus toxoid with aluminum salt) with sodium polystyrenesulfonate powder (mean particle size: 40 $\mu$m), to a final concentration of 0.5 g/ml of carrier. 0.5 ml of this suspension is sprayed or administered by drops into the human nasal cavity.

Example 9

An aqueous suspension was obtained by mixing for 1 hr., 2 L of recombinant Type-B hepatitis vaccine (20 $\mu$m/ml recombinant HB$_s$ antigen protein) with sodium polystyrenesulfonate powder prepared according to the Pharmacopoeia of Japan (mean particle size: 40 $\mu$m) to a final concentration of 0.5 g/ml of carrier. 0.5 ml of this suspension is sprayed or administered by drops into the human nasal cavity.

Example 10

Into an agate ball mill mortar were placed 100 g of dried BCG (Bacillus Calmette-Guerin) vaccine powder and 100 g of calcium polystyrenesulfonate powder (mean particle size: 40 $\mu$m) at a relative humidity of 30 to 40%, and the resulting mixture was uniformly stirred for 10 min. at a relative humidity of 30 to 40%. Then 200 g additional carrier powder was added thereto with stirring for 20 min., followed by 200 g more of this carrier powder and another 20 min. of stirring to produce a medicament of this invention. Approximately 60 mg (corresponding to 12 mg of BCG vaccine) of this mixture was encapsulated in a hard gelatin capsule (capsule No. 4 of the Pharmacopoeia of Japan), which was wrapped in PTP, and placed in an aluminum bag.

Example 11

Into an agate ball mill mortar were placed $8\times10^7$TCID$_{50}$ of dried powder of live attenuated rubella vaccine and 200 g of calcium polystyrenesulfonate powder (mean particle size: 40 $\mu$m), and the resulting mixture was uniformly stirred for 10 min. at a relative humidity of 30 to 40%. Then, 20 g additional carrier powder was added thereto with stirring for 20 min., followed by 200 g more of this carrier powder and another 20 min. of stirring. Finally, 560 g more carrier powder was added with another 20 min. of stirring to produce a medicament of this invention. Approximately 25 mg (corresponding to 2,000 TCID$_{50}$) of this mixture was encapsulated in a hard gelatin capsule (capsule No. 4 of the Pharmacopoeia of Japan), which was wrapped in PTP, and placed in an aluminum bag.

Example 12

Into an agate ball mill mortar were placed 40 g of insulin powder and 200 g of sodium polystyrenesulfonate powder prepared according to the Pharmacopoeia of Japan (mean particle size: 40 μm), and the resulting mixture was uniformly stirred for 10 min. at a relative humidity of 30 to 40%. 560 g more carrier powder was added thereto, followed by stirring for 20 min. to produce a medicament of this invention. Approximately 25 mg (corresponding to 25 units of insulin) of this mixture was encapsulated in a hard gelatin capsule (capsule No. 4 of the Pharmacopoeia of Japan), which was wrapped in PTP, and placed in an aluminum bag. This medicament is nasally administered by means of PABULIZER.

Example 13

Into an agate ball mill mortar were placed 40 g of insulin powder and 200 g powder of Amberlite® IRP64 (mean particle size: 38 μm), and the resulting mixture was uniformly stirred for 10 min. at a relative humidity of 30 to 40%. A further 200 g of this carrier powder was added thereto with stirring for 20 min. Then, 560 g more of this carrier powder was added thereto, and the resulting mixture was stirred for 20 min. to produce a medicament of this invention. Approximately 25 mg (corresponding to 25 units of insulin) of this mixture was encapsulated in a gelatin hard capsule (capsule No. 4 of the Pharmacopoeia of Japan), which was wrapped in PTP, and placed in an aluminum bag. This medicament is nasally administered by means of PABULIZER.

Example 14

Into an agate ball mill mortar were placed 30 g of buserelin acetate and 300 g of Amberlite® IRP64 powder (mean particle size: 38 μm), and the resulting mixture was uniformly stirred for 10 min. at a relative humidity of 30 to 40%. Then, an additional 200 g of carrier powder was added thereto, with stirring for 20 min. Another 2,500 g of this carrier powder was added and the resulting mixture was again stirred for 20 min. to produce a medicament of this invention. Approximately 30 mg (corresponding to 300 μg of buserelin acetate) of this mixture was encapsulated in a hard gelatin capsule (capsule No. 4 of the Pharmacopoeia of Japan), which was wrapped in PTP, and placed in an aluminum bag.

Example 15

Into an agate ball mill mortar were placed 100 g of glucagon and 500 g of sodium polystyrenesulfonate powder prepared according to the Pharmacopoeia of Japan (mean particle size: 40 μm), and the resulting mixture was uniformly stirred for 30 min. at a relative humidity of 40 to 50%. 400 g additional carrier powder was then added thereto, with stirring for 20 min. Finally, 300 g more of this carrier powder was added, and the resulting mixture was stirred for 20 min. to produce a medicament of this invention. Approximately 40 mg (corresponding to 1,000 μg of glucagon) of this mixture was encapsulated in a hard gelatin capsule (capsule No. 4 of the Pharmacopoeia of Japan), which was wrapped in PTP, and placed in an aluminum bag.

Example 16

Into an agate ball mill mortar were placed 40 g of insulin powder and 200 g of styrenedivinylbenzene (Diaion® HP) powder (mean particle size: 40 μm), and the resulting mixture was uniformly stirred for 10 min. at a relative humidity of 30 to 40%. Then, 200 g additional carrier powder was added thereto, with stirring for 20 min., followed by 560 g more carrier powder and another 20 min. of stirring to produce a medicament of this invention. Approximately 25 mg (corresponding to 25 units of insulin) of this mixture was encapsulated in a hard gelatin capsule (capsule No. 4 of the Pharmacopoeia of Japan), which was wrapped in PTP, and placed in an aluminum bag.

Example 17

Into an agate ball mill mortar were placed 40 g of insulin powder and 200 g of styrenedivinylbenzene (Diaion® HP) powder (mean particle size: 40 μm), and the resulting mixture was uniformly stirred for 10 min. at a relative humidity of 30 to 40%. Then, 10 g of hydroxypropylmethylcellulose and 190 g of the carrier powder were added thereto, with stirring for 20 min., and 560 g additional carrier powder was next added, followed by another 20 min. of stirring to produce a medicament of this invention. Approximately 25 mg (corresponding to 25 units of insulin) of this mixture was encapsulated in a hard gelatin capsule (capsule No. 4 of the Pharmacopoeia of Japan), which was wrapped in PTP, and placed in an aluminum bag.

Example 18

Into an agate ball mill mortar were placed 30 g of buserelin acetate and 300 g of Amberlite® IRP64 powder (mean particle size: 38 μm), and the resulting mixture was uniformly stirred for 10 min. at a relative humidity of 30 to 40%. 200 g additional carrier powder was added thereto with stirring for 20 min. Then, 2,500 g more of this carrier powder and 0.2 g of menthol were added thereto, and the resulting mixture was stirred for 20 min. to produce a medicament of this invention. Approximately 30 mg (corresponding to 300 μg of buserelin acetate) of this mixture was encapsulated in a hard gelatin capsule (capsule No. 4 of the Pharmacopoeia of Japan), which was wrapped in PTP, and placed in an aluminum bag.

Example 19

Into an agate ball mill mortar were placed 40 g of insulin and 200 g powder of Amberlite® IRP64 (mean particle size: 38 μm), and the resulting mixture was uniformly stirred for 10 min. at a relative humidity of 30 to 40%. A further 200 g of this carrier powder was added thereto, with stirring for 20 min. Finally, 200 g more of carrier powder was added and the resulting mixture was stirred for 20 min. To the resulting powder was added 360 g of fatty acid glycerin ester to produce a medicament of this invention. Approximately 25 mg (corresponding to 25 units of insulin) of this mixture is administered by drops into the nasal cavity.

Example 20

40 g of insulin powder, 40 g of gelatin, and 100 ml of water were uniformly mixed and the resulting mixture was freeze-dried to powder. The resulting powder and 160 g of Amberlite® IRP64 powder (mean particle size: 38 μm) were placed into an agate ball mill mortar and the mixture was uniformly stirred for 10 min. at a relative humidity of 30 to 40%. Subsequently, the same procedures as in Example 13 were carried out to produce a medicament of this invention. Approximately 25 mg (corresponding to 25 units of insulin) of this mixture was encapsulated in a hard gelatin capsule (capsule No. 4 of the Pharmacopoeia of Japan), which was wrapped in PTP, and placed in an aluminum bag.

The embodiments of the invention in which an exclusive property or privilege is claimed are defined as follows:

1. A medicament suspension or powder for nasal administration to deliver a vaccine or pharmacologically active peptide across the mucous membrane, comprising a powder of one or more cation exchange resins and/or one or more adsorbent resins, to which a vaccine or a pharmacologically active peptide is compounded, the particles of said powder functioning as carriers of said vaccine or peptide during administration of said medicament, wherein said cation exchange resins are selected from the group consisting of polystyrene-sulfonates, polystyrene-acid copolymers, and salts thereof.

2. A medicament for nasal administration as set forth in claim 1, wherein the mean particle size of said powder is not larger than 200 µm.

3. A medicament for nasal administration as set forth in claim 1, wherein said vaccine is a disease agent selected from the group consisting of diphtheria, pertussis, measles, rubella, influenza, Japanese encephalitis, Weil's disease, cholera, mumps, varicella, viral hepatitis, tetanus, and BCG.

4. A medicament for nasal administration as set forth in claim 1, wherein said pharmacologically active peptide is selected from the group consisting of peptide hormones, physiologically active proteins, and enzyme proteins.

5. A medicament for nasal administration as set forth in claim 1, wherein said pharmacologically active peptide is selected from the group consisting of insulin, calcitonin, elcatonin, salmon calcitonin, buserelin acetate (Gn-RH derivative), leuprorelin acetate (LH-RH derivative), somatropin, and glucagon.

6. A medicament for nasal administration as set forth in claim 1, wherein a mixture comprising said vaccine or pharmacologically active peptide, and a substance selected from the group consisting of salts, proteins, amino acids, and sugars, is compounded to said cation exchange resin or adsorbent resin powder.

7. A medicament for nasal administration as set forth in claim 1, which comprises one or more substances selected from the group consisting of buffers, smoothing agents, powdered water-soluble polymers, fats, polyhydric alcohols, powdered sugars, powdered amino acids, water-soluble acids, bases, and salts thereof, perfumes, and chelating agents.

8. A medicament for nasal administration as set forth in claim 1, wherein the mean particle size of said powder is not larger than 200 µm.

9. A medicament for nasal administration as set forth in claim 1, wherein a mixture comprising said vaccine or pharmacologically active peptide, and a substance selected from the group consisting of salts, proteins, amino acids, and sugars, is compounded to said cation exchange resin or adsorbent resin powder.

10. A medicament for nasal administration as set forth in claim 1, which comprises one or more substances selected from the group consisting of buffers, smoothing agents, powdered water-soluble polymers, fats, polyhydric alcohols, powdered sugars, powdered amino acids, water-soluble acids, bases, and salts thereof, perfumes, and chelating agents.

11. A method for trans-mucous membrane administration of vaccines and pharmacologically active peptides comprising spraying or administering by drops into the nasal cavity a composition comprising a powder of one or more cation exchange resins and/or one or more adsorbent resins, to which a vaccine or a pharmacologically active peptide is compounded, the particles of said powder functioning as carriers of said vaccine or peptide, wherein said cation exchange resins are selected from the group consisting of polystyrene-sulfonates, polystyrene-acid copolymers, and salts thereof.

12. A method according to claim 1 wherein the mean particle size of said powder is not larger than 200 µm.

13. A method according to claim 11 wherein said vaccine is a disease agent selected from the group consisting of diphtheria, pertussis, measles, rubella, influenza, Japanese encephalitis, Weil's disease, cholera, mumps, varicella, viral hepatitis, tetanus, and BCG.

14. A method according to claim 11 wherein said pharmacologically active peptide is selected from the group consisting of peptide hormones, physiologically active proteins, and enzyme proteins.

15. A method according to claim 11 wherein said pharmacologically active peptide is selected from the group consisting of insulin, calcitonin, elcatonin, salmon calcitonin, buserelin acetate (Gn-RH derivative), leuprorelin acetate (LH-RH derivative), somatropin, and glucagon.

16. A method according to claim 11 wherein a mixture comprising said vaccine or pharmacologically active peptide, and a substance selected from the group consisting of salts, proteins, amino acids, and sugars, is compounded to said cation exchange resin or adsorbent resin powder.

17. A method according to claim 11 wherein a mixture comprising said vaccine or pharmacologically active peptide, and a substance selected from the group consisting of salts, proteins, amino acids, and sugars, is compounded to said cation exchange resin or adsorbent resin powder.

18. A method according to claim 11 wherein the administered medicament comprises once or more substances selected from the group consisting of buffers, smoothing agents, powdered water-soluble polymers, fats, polyhydric alcohols, powdered sugars, powdered amino acids, water-soluble acids, bases, and salts thereof, perfumes, and chelating agents.

19. A method according to claim 16 wherein the administered medicament comprises one or more substances selected from the group consisting of buffers, smoothing agents, powdered water-soluble polymers, fats, polyhydric alcohols, powdered sugars, powdered amino acids, water-soluble acids, bases, and salts thereof, perfumes, and chelating agents.

* * * * *

UNITED STATES PATENT AND TRADEMARK OFFICE
CERTIFICATE OF CORRECTION

PATENT NO. : 5,942,242
DATED : August 24, 1999
INVENTOR(S) : Mizushima et al.

It is certified that error appears in the above-identified patent and that said Letters Patent is hereby corrected as shown below:

On the title page

[75] Inventors:
    Tetsuo Ebata, "Kunitachi" should be Tetsuo Ebata, --Tokyo--.

*Column 5, line 48;
    "humility" should be --humidity--.

*Column 5, line 60;
    "means" should be --mean--.

*Column 5, line 63;
    "(Diaion HP10)" should be --(Diaion® HP10)--.

*Column 6, line 25;
    "an 0.5 g/ml carrier" should be --a 0.5 g/ml carrier--.

UNITED STATES PATENT AND TRADEMARK OFFICE
CERTIFICATE OF CORRECTION

PATENT NO. : 5,942,242
DATED : August 24, 1999
INVENTOR(S) : Mizushima et al.

It is certified that error appears in the above-identified patent and that said Letters Patent is hereby corrected as shown below:

Column 12, Claim 12, line 18;
    "claim 1" should be --claim 11--.

Column 12, Claim 18, line 46;
    "once" should be --one--.

Column 12, Claim 19, line 52;
    "claim 16" should be --claim 11--.

Signed and Sealed this

Second Day of May, 2000

Attest:

Q. TODD DICKINSON

*Attesting Officer*      *Director of Patents and Trademarks*